United States Patent

Persson

[11] Patent Number: 6,018,988
[45] Date of Patent: Feb. 1, 2000

[54] METHOD AND DEVICE IN A RHEOMETER

[75] Inventor: Leif Persson, Staffanstorp, Sweden

[73] Assignee: Hansson Thyresson Patentbyra AB, Malmo, Sweden

[21] Appl. No.: 09/029,194

[22] PCT Filed: Jun. 26, 1997

[86] PCT No.: PCT/SE97/01159

§ 371 Date: Feb. 25, 1998

§ 102(e) Date: Feb. 25, 1998

[87] PCT Pub. No.: WO97/49981

PCT Pub. Date: Dec. 31, 1997

[30] Foreign Application Priority Data

Jun. 26, 1996 [SE] Sweden .................................. 9602517

[51] Int. Cl.⁷ .................................................. G01N 11/10
[52] U.S. Cl. ......................................... 73/54.25; 73/54.41
[58] Field of Search ............................... 73/54.24, 54.25, 73/32 A, 54.26, 54.37, 54.14, 54.34

[56] References Cited

U.S. PATENT DOCUMENTS

| 3,393,553 | 7/1968 | Kleinschmidt | 73/54.24 |
| 3,777,550 | 12/1973 | Kleinschmidt | 73/54.24 |
| 4,292,673 | 9/1981 | DuBae | 702/54 |

FOREIGN PATENT DOCUMENTS

| 0014164 | 8/1981 | European Pat. Off. |
| 842 491 | 7/1981 | U.S.S.R. |
| WO 88.03264 | 5/1988 | WIPO |
| WO 88/0326 | 5/1988 | WIPO ............................ G01N 11/00 |

*Primary Examiner*—Hezron Williams
*Assistant Examiner*—Jay L. Politzer
*Attorney, Agent, or Firm*—Mathews, Collins, Shepherd & Gould, P.A.

[57] ABSTRACT

A method for determining the rheological properties of a sample substance by the use of a rheometer, in which at least one element having magnetoelastic characteristics is received in said sample substance. The element is set into mechanical oscillation by the influence of a magnetic field and its oscillation characteristics are determined by the effect exerted by the oscillation of the element on an outer magnetic field which, in turn, provides information regarding the rheological properties of the sample substance. The device comprises a receptacle for the sample substance and the element. An exciting coil array is provided for exciting the element, thus causing it to oscillate mechanically; and a sensing coil array is provided to register the effect of the element on an existing magnetic field image during oscillation of the element. A calculation unit is operatively engaged with the sensing coil array for determining the oscillation characteristics of the element and therefrom deriving the rheological properties of the sample substance.

13 Claims, 1 Drawing Sheet

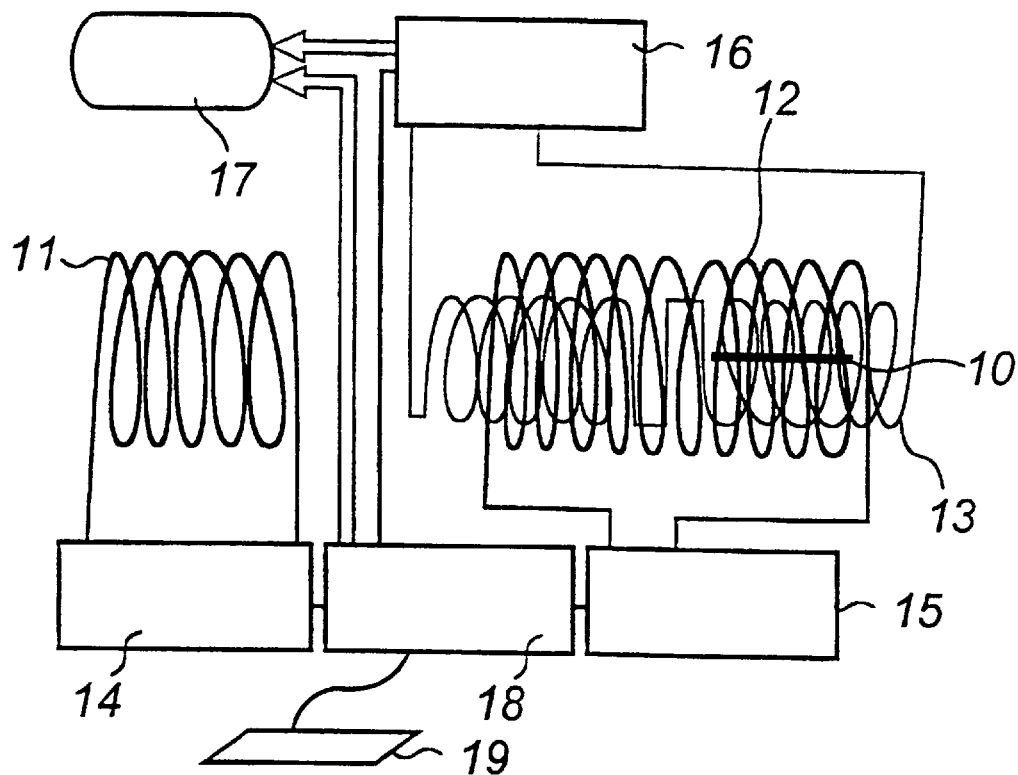
FIG 1
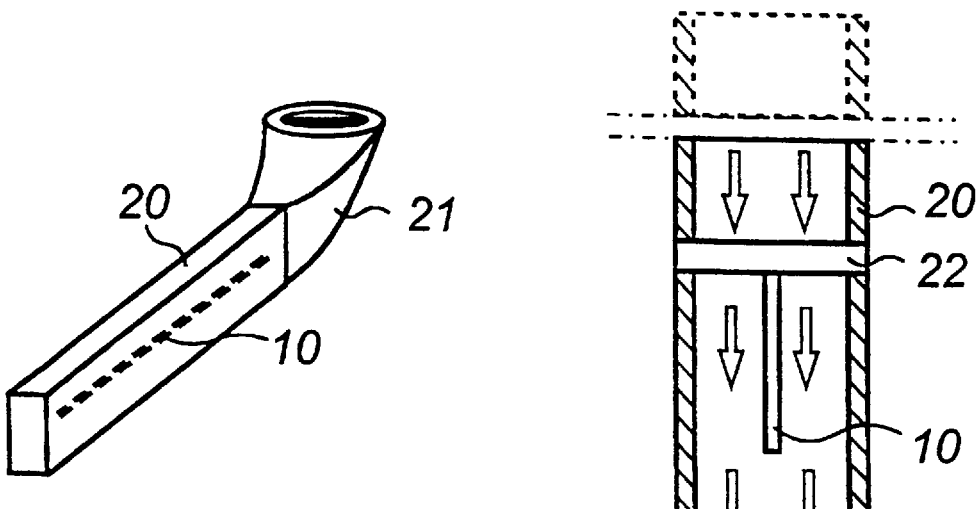
FIG 2
FIG 3

METHOD AND DEVICE IN A RHEOMETER

TECHNICAL FIELD OF THE INVENTION

The invention concerns a method and a device regarding use of a rheometer for determining the rheological properties of a fluid. Viscoelastic and rheological properties of fluids, liquids and other substances are measured under various conditions, so that, in certain cases, these properties will comply with certain requirements and guidelines. In other instances, the reason being determination of a feature associated with these properties.

STATE OF THE ART

When a fluid's rheological properties are measured, a variety of rheometers and other rheological instruments are used. Such measuring equipment usually comprises two measuring bodies between which a test sample is placed. By rotating the measuring bodies in relation to each other, the capability of the sample to transfer momentum is a way to measure the desired property.

It is a problem, however, that a relatively large amount of sample substance is required. It is also a drawback that the measuring bodies have to be carefully cleaned between different measurements. These problems are particularly obvious when a great number of measurements are to be conducted, or when they need to be carried out intermittently or continuously. Examples of fluids for which these problems arise are body liquids such as for instance blood, synovial fluid, saliva, lymph fluid, etc.

Another type of device used for viscosity measurements is found in SU 842941, which presents and describes a method and a device for viscosity measurement of primarily victuals. A screw-wound element of magnetostrictive material is inserted in a receptacle such that the ends of the element extend out of the receptacle. A first coil encloses a projecting first end, and a second coil encloses the projecting second end for sensing the oscillation frequency of the element. The detected oscillation frequency is registered by an electronic device. In certain applications it is disadvantageous that the element must be accessible external to the receptacle.

To measure in accord with the in-line type, that is during an ongoing process, cannot be done in practice using methods hitherto known. It would be desirable for example in the food industry to be able to continuously or repeatedly discharge a sample from a fluid flow and to carry out the measurement.

THE INVENTION IN SUMMARY

It is an object of the invention to essentially eliminate the abovementioned problems and drawbacks. This object is achieved by imparting the features specified in patent claims 1 and 2, respectively, to the invention. Additional objects and advantages of the invention are obvious from the accompanying description, drawing and patent claims.

For the measurement, use is made of strips, wires or other elements of amorphous material having definite magneto-mechanical and magnetoelastical properties. Various amorphous alloys, for instance METGLASS, are very suitable in this context. The element is positioned in a receptacle together with the sample whose properties are to be measured. The receptacle is brought into a measuring area which presents certain magnetic conditions, by means of which the element is set into mechanical oscillation. The oscillation frequency of the element is measured by the element's effect on an external magnetic field, and the sample's rheological properties are determined by the measured oscillation frequency of the element. For continuous measurements, among other things, the receptacle can be designed as part of a pipeline or as a bypass of the pipeline, through which the sample is passed.

The invention allows for measurement without the need to reuse mobile parts. Thus, there is no need for preparation of such parts. The measuring cycle will also be very short, a typical value being 1–2 minutes. Multiple measurements can be carried out for the same sample, and it is also possible to conduct several measurements simultaneously.

BRIEF DESCRIPTION OF THE DRAWINGS

The invention will now be described in more detail using exemplary embodiments with reference to the accompanying drawings, in which FIG. 1 is a principal view of a practical embodiment of a device in accord with the invention, FIG. 2 represents a perspective view of a receptacle used in one embodiment of the invention, and FIG. 3 shows a sectional view of a receptacle according to an alternate embodiment of the invention.

DESCRIPTION

The principle of measurement according to the invention becomes evident from FIG. 1. An element 10 is positioned within the working area of a coil system comprising multiple coil arrays. A first coil array 11 is employed to generate a magnetic bias field which sets up element 10 for the succeeding step of measurement. Preferably the bias field is static. For distinguishing and identification purposes, however, bias fields may also be used that vary in correspondence to a function. Instead of a coil array 11 one or several permanent magnets can be used.

A second coil array 12 is employed to excite element 10, causing it to oscillate mechanically. Preferably, element 10 is excited to mechanical self-oscillation when a signal having sweep frequency varying between low kHz to a few hundred kHz is applied to coil array 12. The shape of the curve of the signal and its frequency range vary depending on both prevailing measuring conditions and those properties that are to be measured.

A third coil array 13 is employed to detect changes in the magnetic field within the working area of the coil system. Preferably, the third coil array 13 is configured with two coils of opposing windings; element 10 is intended to affect only one of these. Trimming and calibration of the measuring arrangement is thereby facilitated. The mechanical oscillation of the element gives rise to a magnetically alternating field, the properties of which are sensed by the third coil array 13. The properties of the magnetically alternating field are related to the magnetomechanical properties of the element, for example its natural oscillation. The magnetomechanical properties of the element 13 are, in turn, affected by the rheological and viscoelastical properties of the sample substance. A high viscosity of the sample substance most often damps the oscillations and therefore lowers the natural frequency of the element 10. Under certain special circumstances the viscosity of a sample substance may affect the oscillations in a more complex manner.

It is also important to note that elements of this type may oscillate in various ways. There is for instance longitudinal oscillation, but also transversal and torsional oscillations. The various oscillation types interact in certain cases, raising the demands on the analysis of the measurement result.

The first coil array is driven and governed by a first control unit 14, which is configured to generate a bias field that is appropriate for the application. A second control unit 15 drives and governs the exciting coil array 12 such that this puts element 10 into oscillation. The third coil array 13 is connected to a measuring and analysis unit 16, in which the detected changes in the magnetic field are measured and analyzed for determination of the rheological properties of the sample substance. Measuring and analysis unit 16 is operationally connected to a display unit 17, on which the measurement result can be presented in an adequate way.

In the embodiment as per FIG. 1, the control units 14 and 15 as well as the measuring and analysis unit 16 are operationally connected to a central unit 18. This can be used to monitor and control both measurement and calibration of the entire measuring device. A keyboard 19 or any other type of input unit is used by the operator to control measuring and similar processes.

In a practical embodiment, element 10 is inserted in a receptacle 20. Receptacle 20 is made of non-magnetic material, for example glass or similar. The shape is preferably adapted to that of element 10. Advantageously, element 10 is made as a straight flat strip or a straight wire. The volume contained in receptacle 20 is comparatively small. The sample substance, however, should surround element 10 during measurement in order to achieve the most reliable result. Receptacle 20 is equipped with some kind of connector 21 for the insertion of the sample substance. The receptacle may be designed in other completely different ways, for instance as a syringe or similar, into which the sample substance is directly aspirated during sampling.

In the embodiment as per FIG. 3, receptacle 20 is designed as a tubing. The tube may be part of a pipeline, through which a flow of the sample substance normally passes in a production process or similar. It may also be appropriate to design the tube as part of a bypass for the normal flow such that a minor portion of the flow bypasses the tube and element 10.

Element 10 should be enclosed by the sample substance or at least be substantially covered by the sample substance so that the effect on element 10 becomes uniform and reiterative. In the embodiment as per FIG. 3, the element is centrally suspended in the tube by fastening means 22 provided within the tube.

The resonance frequency of element 10 varies depending on the viscosity of the sample substance. In air, the oscillation is essentially undamped, whereas, in most cases, it adopts an increasingly lower frequency as the viscosity of the sample substance gets higher. By determining, in advance, the resonance frequency of element 10 in air, or in a medium with known viscosity and other rheological, known properties, or by using calibrated elements 10, measuring the resonance frequency of element 10 in a sample substance provides data to determine said properties for the sample substance. It is also possible to measure the resonance frequency for several different elements 10 in the same sample substance and, thus, allow for the determination of the sample substance viscosity relative to the frequency/velocity.

The measuring and analysis unit 16 preferably comprises means for monitoring phase change of the signal received. There is namely in the type of elements used a strong phase shift during transition to self-oscillation. It is also possible to record the resonance frequency during the strong displacement of the signal level which occurs at self-oscillation. The signal level or the amplitude or other oscillation characteristics per se may also be utilized for the measurement, since it is also affected by the rheological properties of the sample. It should therefore be possible to conduct measurement at a frequency other than that of self-oscillation.

What is claimed is:

1. A method for determining, by the use of a rheometer, the rheological properties of a sample substance comprising the steps of:
    receiving at least one element having magnetoelastic characteristics in said sample substance, said element is a straight elongated strip or wire and is completely enclosed by said sample substance;
    subjecting said element to a magnetic bias field;
    exciting said element into mechanical oscillation by the influence of a second magnetic field;
    determining the oscillation characteristics of said element by the effect of said element oscillation on a third magnetic field; and
    determining rheological properties of the sample substance from the measured oscillation characteristics of said element.

2. The method as claimed in claim 1, wherein said step of receiving at least one element comprises the steps of:
    inserting said at least one element in a receptacle, and
    inserting said sample substance in said receptacle.

3. The method as claimed in claim 1 wherein said step of exciting said element comprises the step of:
    applying an excitation coil array to said element to excite said element; and
    wherein said step of determining the oscillation characteristics comprises the step of:
    magnetically connecting said excitation coil array to a sensing coil array to sense magnetic field changes caused by said element.

4. The method as claimed in claim 1 wherein said magnetic bias field is generated by a biasing coil array.

5. The method as claimed in claim 1 wherein the oscillation frequency of said element is used as said oscillation characteristics.

6. The method as claimed in claim 1 wherein said element is brought to oscillate at its natural oscillation frequency.

7. The method as claimed in claim 1 wherein a measured signal level of said sensing coil array is used as oscillation characteristics at a certain oscillation frequency of said element.

8. A device regarding rheometers for determining the rheological properties of a sample substance comprising:
    a receptacle for receiving the sample substance, said receptacle receives at least one element of amorphous material in such a way that said element is completely enclosed by said sample substance in said receptacle;
    means for generating a magnetic bias field across said element;
    an exciting coil array for excitation of said at least one element so as to cause it to oscillate mechanically;
    a sensing coil array for recording of the effect of said element on an existing magnetic field image during oscillation of said element; and a calculation unit operatively connected to said sensing coil array for determining the oscillation characteristics of said element and therefrom deriving the rheological properties of the sample substance.

9. The device as claimed in claim 8 wherein said means for generating a magnetic field comprises a biasing coil array.

10. The device as claimed in claim 9 wherein said means for generating a magnetic field is operatively connected to a first control unit.

11. The device as claimed in claim 10 wherein said exciting coil array is operatively connected to a second control unit and said second control unit supplies a frequency sweep signal to said exciting coil array.

12. The device as claimed in claim 8 wherein said receptacle comprises a tubing for reception of a flow of said sample substance, and said exciting coil array and said sensing coil array are arranged around said tubing.

13. The method of claim 1 wherein said element oscillates in longitudinal oscillation, transversal oscillation and torsinal oscillation.

* * * * *

UNITED STATES PATENT AND TRADEMARK OFFICE
CERTIFICATE OF CORRECTION

PATENT NO.    : 6,018,988
DATED         : February 1, 2000
INVENTOR(S)   : Leif Persson It is certified that error appears in the above-identified patent and that said Letters Patent is hereby corrected as shown below:

<u>Title page,</u>
Item [73], Assignee should be: -- Protell AB, Lund, Sweden --

Signed and Sealed this

Thirtieth Day of July, 2002

*Attest:*

*Attesting Officer*

JAMES E. ROGAN
*Director of the United States Patent and Trademark Office*